US012725356B2

(12) United States Patent
Mazumder et al.

(10) Patent No.: US 12,725,356 B2
(45) Date of Patent: Sep. 1, 2026

(54) COMPUTATIONAL MODEL TO PERSONALIZE DEFIBRILLATION MECHANISM OF WEARABLE CARDIAC DEFIBRILLATOR

(71) Applicant: Tata Consultancy Services Limited, Mumbai (IN)

(72) Inventors: Oishee Mazumder, Kolkata (IN); Aniruddha Sinha, Kolkata (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 1257 days.

(21) Appl. No.: 17/583,442

(22) Filed: Jan. 25, 2022

(65) Prior Publication Data

US 2022/0237870 A1 Jul. 28, 2022

(30) Foreign Application Priority Data

Jan. 27, 2021 (IN) ............................ 202121002803

(51) Int. Cl.

| | |
|---|---|
| ***G01N 33/48*** | (2006.01) |
| ***A61N 1/36*** | (2006.01) |
| ***G06T 7/11*** | (2017.01) |
| ***G06T 17/20*** | (2006.01) |
| *G16H 40/63* | (2018.01) |

(52) U.S. Cl.

CPC .......... *G06T 17/20* (2013.01); *A61N 1/36031* (2017.08); *G06T 7/11* (2017.01); *G06T 2207/10088* (2013.01); *G06T 2207/30048* (2013.01); *G16H 40/63* (2018.01)

(58) Field of Classification Search

None

See application file for complete search history.

(56) References Cited

PUBLICATIONS

Mazumder, Oishee, and Aniruddha Sinha. "In silico evaluation of wearable cardiac defibrillator: personalized therapy planning to prevent sudden cardiac death." 2021 29th European Signal Processing Conference (EUSIPCO). IEEE, 2021.*

Jorgenson, D. Blilie, et al. "Computational studies of transthoracic and transvenous defibrillation in a detailed 3-D human thorax model." IEEE transactions on biomedical engineering 42.2 (1995): 172-184.*

Jolley, Matthew, et al. "Finite element modeling of subcutaneous implantable defibrillator electrodes in an adult torso." Heart rhythm 7.5 (2010): 692-698.*

Jolley et al., "A Computer Modeling Tool for Comparing Novel ICD Electrode Orientations in Children and Adults," Heart Rhythm, 5(4):565-572 (2008).

Triedman et al., "A System for Image Based Finite Element Modeling of Novel Defibrillation Strategies," (2008).

* cited by examiner

*Primary Examiner* — Anna Skibinsky

(74) *Attorney, Agent, or Firm* — FINNEGAN, HENDERSON, FARABOW, GARRETT & DUNNER LLP

(57) ABSTRACT

This disclosure relates generally to a computational model for personalizing defibrillation mechanism of wearable cardiac defibrillator (WCD). Cardiac defibrillators are lifesaving therapeutic device with potentially harming capacity if not tuned properly. Hence creation of a personalized energy distribution model based on subject's anatomy, rather than a 'one size fits all' approach is preferred. The disclosed model compares the efficiency of standard and nonstandard WCD electrode placement in the torso vest, demonstrating significant differences in defibrillation efficacy associated with different strategies. A new measure is presented for performing such a comparison which combines the DFT and extent of myocardial damage.

11 Claims, 7 Drawing Sheets

MODEL, FOR EACH OF THE PLURALITY OF BIOPHYSICAL MODELS, MYOCARDIAL POTENTIAL GRADIENT (M) BY USING A FINITE ELEMENT METHOD (FEM) VIA THE ONE OR MORE HARDWARE PROCESSORS, WHEREIN THE MYOCARDIAL POTENTIAL GRADIENT IS INDICATIVE OF AN EFFECT OF VOLTAGES APPLIED AT THE SET OF ELECTRODES DURING DEFIBRILLATION

206

COMPUTE, FOR EACH OF THE PLURALITY OF BIOPHYSICAL MODELS, AN IDEAL PROBABILISTIC DISTRIBUTION OF MYOCARDIAL VOLTAGE GRADIENT (C) AFTER DEFIBRILLATION BY COMBINING A FIRST EXPONENTIAL FUNCTIONS RISING IN AMPLITUDE FOR BELOW A PREDETERMINED VOLTAGE GRADIENT AND A SECOND EXPONENTIAL FUNCTION DECAYING IN AMPLITUDE FOR BELOW THE PREDETERMINED VOLTAGE GRADIENT VIA THE ONE OR MORE HARDWARE PROCESSORS

208

CALCULATE, FOR EACH OF THE PLURALITY OF THE BIOPHYSICAL MODELS, A DIVERGENCE IN THE DISTRIBUTION OF THE MYOCARDIAL POTENTIAL GRADIENT (M) WITH RESPECT TO THE IDEAL PROBABILISTIC DISTRIBUTION OF THE MYOCARDIAL VOLTAGE GRADIENT (C) VIA THE ONE OR MORE HARDWARE PROCESSORS

210

SELECT, VIA THE ONE OR MORE HARDWARE PROCESSORS, A BIOPHYSICAL MODEL FROM AMONGST THE PLURALITY OF BIOPHYSICAL MODELS BASED ON THE CALCULATION OF THE DIVERGENCE

212

COMPUTATIONAL MODEL TO PERSONALIZE DEFIBRILLATION MECHANISM OF WEARABLE CARDIAC DEFIBRILLATOR

PRIORITY CLAIM

This U.S. patent application claims priority under 35 U.S.C. § 119 to: India Application No. 202121002803, filed on Jan. 27, 2021. The entire contents of the aforementioned application are incorporated herein by reference.

TECHNICAL FIELD

The disclosure herein generally relates to cardiac defibrillator, and, more particularly, to computational model for generating a computational model to predict and optimize defibrillation mechanism of a Wearable Cardiac Defibrillator (WCD).

BACKGROUND

Sudden cardiac death (SCD) is an unpredictable event causing around 13% of deaths in the overall population and about 36% of deaths in heart failure patients. Leading cause of SCD is attributed to ventricular arrhythmia (VA), ventricular fibrillation (VF) associated with acute myocardial ischemia. VF is usually lethal within minutes of its inception and if not immediately treated, leads to cardiac arrest. Electrical defibrillation is the only effective therapy for cardiac arrest caused by ventricular fibrillation (VF).

Due to the prompt action requirement in VF leading to SCD, implantable cardioverter defibrillator (ICD) is the popular choice for treatment of SCD. Risk of SCD is usually predicted based on left ventricular ejection fraction (LVEF). For patients recovering from myocardial infraction or newly diagnosed heart failure, LVEF may improve with treatment and even though SCD is a possibility, ICD implantation may not be the best treatment plan. Being an invasive process along with the cost and its effect on quality of life, ICD implantation requires a rigorous patient evaluation and is only recommended when absolutely required. WCD is usually recommended to patients awaiting ICD, patients with ventricular assist device awaiting heart transplantation or in recovery phase after nonischemic cardiomyopathy. WCD requires no surgical intervention, completely removable and has been shown to be equally efficient in terminating VA by defibrillation shocks.

Irrespective of the type of defibrillator, strong shocks required during defibrillation have serious adverse effects on myocardium property like change in contractility, mechanical dysfunction affecting hemodynamics along with the possibility of ectopic excitation after depolarization initiating post shock arrhythmia. Hence, it is extremely important to tune and optimize the shock energy to get the desired effect. Computational model analyzing defibrillation mechanism and the aftereffect of shock voltage in myocardium provides in-depth understanding and helps in optimizing the defibrillation threshold. Distribution of electric field in the heart is closely related to the nature of defibrillation. Defibrillation shock should be able to depolarize the heart homogeneously, without initiating reentry of wave fronts associated with the electric field.

SUMMARY

Embodiments of the present disclosure present technological improvements as solutions to one or more of the above-mentioned technical problems recognized by the inventors in conventional systems. For example, in one embodiment, a processor-implemented method for generating a computational model to predict and optimize defibrillation mechanism of a Wearable Cardiac Defibrillator (WCD) is provided. The method includes obtaining imaging scan data associated with subject's torso, the imaging scan data indicative of subject's torso cardiac geometry, via one or more hardware processors. Further, the method includes simulating a plurality of biophysical models of a Wearable Cardiac Defibrillator (WCD) via the one or more hardware processors, each biophysical model of the plurality of biophysical models comprising a distinct configuration of a set of electrodes, the set of electrodes capable of measuring shock voltages from myocardium of the subject's torso using the imaging scan data. Furthermore the method includes modeling, for each of the plurality of biophysical models, myocardial potential gradient (M) by using a Finite Element method (FEM) via the one or more hardware processors, wherein the myocardial potential gradient is indicative of an effect of voltages applied at the set of electrodes during defibrillation. Moreover, the method includes computing, for each of the plurality of biophysical models, a probabilistic distribution of myocardial voltage gradient (C) after defibrillation by combining a first exponential functions rising in amplitude for below a predetermined voltage gradient and a second exponential function decaying in amplitude for below the predetermined voltage gradient via the one or more hardware processors. Also, the method includes calculating, for each of the plurality of the biophysical models, a divergence in the distribution of the myocardial potential gradient (M) with respect to the probabilistic distribution of the myocardial voltage gradient (C) via the one or more hardware processors. The method further includes selecting, via the one or more hardware processors, a biophysical model from amongst the plurality of biophysical models based on the calculation of the divergence.

In another aspect, a system to generate a computational model to predict and optimize defibrillation mechanism of a Wearable Cardiac Defibrillator (WCD) is provided. The system includes a memory storing instructions, one or more communication interfaces; and one or more hardware processors coupled to the memory via the one or more communication interfaces, wherein the one or more hardware processors are configured by the instructions to obtain imaging scan data associated with subject's torso, the imaging scan data indicative of subject's torso cardiac geometry. Further, the one or more hardware processors are configured by the instructions to simulate a plurality of biophysical models of a Wearable Cardiac Defibrillator (WCD), each biophysical model of the plurality of biophysical models comprising a distinct configuration of a set of electrodes, the set of electrodes capable of measuring shock voltages from myocardium of the subject's torso using the imaging scan data. Furthermore, the one or more hardware processors are configured by the instructions to model, for each of the plurality of biophysical models, myocardial potential gradient (M) by using a Finite Element method (FEM), wherein the myocardial potential gradient is indicative of an effect of voltages applied at the set of electrodes during defibrillation. Moreover, the one or more hardware processors are configured by the instructions to compute for each of the plurality of biophysical models, a probabilistic distribution of myocardial voltage gradient (C) after defibrillation by combining a first exponential functions rising in amplitude for below a predetermined voltage gradient and a second exponential function decaying in amplitude for below the predetermined voltage gradient. Also, the one or more hardware processors are configured by the instructions to calculate, for each of the plurality of the biophysical models, a divergence in the distribution of the myocardial potential gradient (M) with respect to the probabilistic distribution of the myocardial voltage gradient (C). Moreover, the one or more hardware processors are configured by the instructions to select a biophysical model from amongst the plurality of biophysical models based on the calculation of the divergence.

In yet another aspect, a non-transitory computer readable medium for method for generating a computational model to predict and optimize defibrillation mechanism of a Wearable Cardiac Defibrillator (WCD) is provided. The method includes obtaining imaging scan data associated with subject's torso, the imaging scan data indicative of subject's torso cardiac geometry, via one or more hardware processors. Further, the method includes simulating a plurality of biophysical models of a Wearable Cardiac Defibrillator (WCD) via the one or more hardware processors, each biophysical model of the plurality of biophysical models comprising a distinct configuration of a set of electrodes, the set of electrodes capable of measuring shock voltages from myocardium of the subject's torso using the imaging scan data. Furthermore the method includes modeling, for each of the plurality of biophysical models, myocardial potential gradient (M) by using a Finite Element method (FEM) via the one or more hardware processors, wherein the myocardial potential gradient is indicative of an effect of voltages applied at the set of electrodes during defibrillation. Moreover, the method includes computing, for each of the plurality of biophysical models, a probabilistic distribution of myocardial voltage gradient (C) after defibrillation by combining a first exponential functions rising in amplitude for below a predetermined voltage gradient and a second exponential function decaying in amplitude for below the predetermined voltage gradient via the one or more hardware processors. Also, the method includes calculating, for each of the plurality of the biophysical models, a divergence in the distribution of the myocardial potential gradient (M) with respect to the probabilistic distribution of the myocardial voltage gradient (C) via the one or more hardware processors. The method further includes selecting, via the one or more hardware processors, a biophysical model from amongst the plurality of biophysical models based on the calculation of the divergence.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles:

FIGS. 2A-2B is a flowchart illustrating a method for generating a computational model to predict and optimize defibrillation mechanism of the WCD according to some embodiments of the present disclosure.

DETAILED DESCRIPTION

Figure 1:
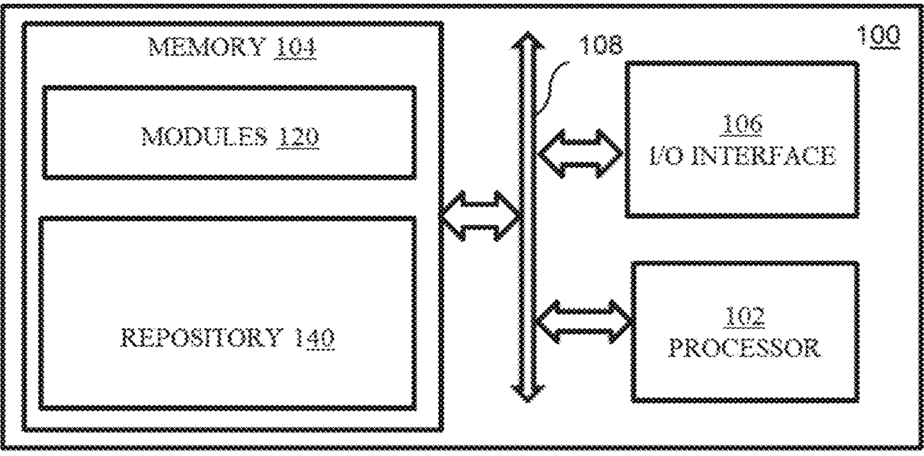
FIG. 1 illustrates an exemplary system for generating a computational model to predict and optimize defibrillation mechanism of a Wearable Cardiac Defibrillator (WCD) according to some embodiments of the present disclosure.

Mathematical modeling and computer simulation can predict the defibrillation effect and help in ICD standardization. Computational cardiac models incorporate the concept of volume conduction and bidomain propagation in cardiac tissues to study the effect of defibrillation in both spatial and temporal domain. These models are computationally extensive and challenging with both time and memory constraints. A rather simple, globally accepted index of defibrillation success is via determining Defibrillation threshold (DFT), which is derived from the critical mass hypothesis. Finite Element (FE) models of defibrillation based has been reported for ICD (both transverse and subcutaneous) along with electrode size optimization for varying patient size using DFT index. However, there are no reported computational model to assess the defibrillation quality and effectiveness of WCD with respect to electrode configuration, voltage and energy requirement for minimal myocardial damage.

Various embodiments described here provides method and system for cardiac computational model for in silico defibrillation evaluation and optimization in terms of electrode configuration for WCD. The disclosed embodiments provide an evaluation measure combining DFT and myocardial damage probability, which would aid in configuring probable shock electrode configurations for WCD performance optimization. The pipeline for subject specific image based FE modeling and evaluation would help in creating personalized WCD settings to reach DFT and minimum myocardial damage configuration. This would result in optimum shock deliver configuration for specific subject anatomy, enabling a personalized therapy approach.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments. It is intended that the following detailed description be considered as exemplary only, with the true scope being indicated by the following claims.

Referring now to the drawings, and more particularly to FIG. 1 through 6, where similar reference characters denote corresponding features consistently throughout the figures, there are shown preferred embodiments and these embodiments are described in the context of the following exemplary system and/or method.

FIG. 1 illustrates an exemplary block diagram of a system 100 for generating a computational model to predict and optimize defibrillation mechanism of a Wearable Cardiac Defibrillator (WCD), in accordance with an embodiment of the present disclosure. The computational model utilizes high resolution torso cardiac magnetic resonance imaging (MRI) followed by biophysical simulation to assess the efficacy of defibrillation by determining defibrillation thresholds (DFT) and extent of myocardial damage. A measure for quantifying such efficacy is disclosed in the embodiments of the present disclosure, whereby the disclosed system 100 calculates the divergence in the distribution of myocardial potential gradient obtained in silico, with respect to an ideal probabilistic distribution, defined for defibrillator success. Variations in defibrillation efficacy is simulated for using different shocking electrode configurations to assess the best defibrillator outcome with minimal myocardial damage. The developed computation model can be used for designing personalized WCD vests depending on subject specific anatomy and pathology, as will be described with reference to the description below.

In an embodiment, the system 100 includes one or more processors 104, communication interface device(s) or input/output (I/O) interface(s) 106, and one or more data storage devices or memory 102 operatively coupled to the one or more processors 104. The one or more processors 104 that are hardware processors can be implemented as one or more microprocessors, microcomputers, microcontrollers, digital signal processors, central processing units, state machines, graphics controllers, logic circuitries, and/or any devices that manipulate signals based on operational instructions. Among other capabilities, the processor(s) are configured to fetch and execute computer-readable instructions stored in the memory. In an embodiment, the system 100 can be implemented in a variety of computing systems, such as laptop computers, notebooks, hand-held devices, workstations, mainframe computers, servers, a network cloud and the like.

The I/O interface device(s) 106 can include a variety of software and hardware interfaces, for example, a web interface, a graphical user interface, and the like and can facilitate multiple communications within a wide variety of networks N/W and protocol types, including wired networks, for example, LAN, cable, etc., and wireless networks, such as WLAN, cellular, or satellite. In an embodiment, the I/O interface device(s) can include one or more ports for connecting a number of devices to one another or to another server.

The memory 102 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. In an embodiment, one or more modules (not shown) of the system 100 can be stored in the memory 102.

In an embodiment, the system 100 includes one or more data storage devices or memory 102 operatively coupled to the one or more processors 104 and is configured to store instructions configured for execution of steps of the method 100 by the one or more processors 104.

Figure 2A:
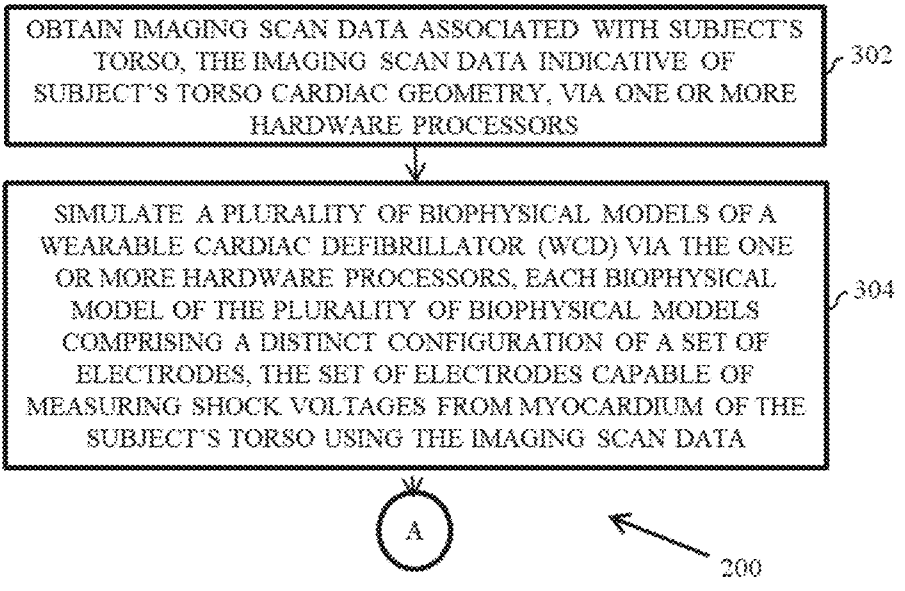

FIGS. 2A-2B is an exemplary flow diagram illustrating a computer implemented method 200 for generating a computational model to predict and optimize defibrillation mechanism of a WCD in accordance with an embodiment of the present disclosure. The steps of the method 200 will now be explained in detail with reference to the components of the system 100 (of FIG. 1) and FIGS. 3 through 6. Although process steps, method steps, techniques or the like may be described in a sequential order, such processes, methods and techniques may be configured to work in alternate orders. In other words, any sequence or order of steps that may be described does not necessarily indicate a requirement that the steps be performed in that order. The steps of processes described herein may be performed in any order practical. Further, some steps may be performed simultaneously.

Initially, an imaging scan (for example, an MRI and/or a CT scan) of a subject may be obtained. The imaging scan may be obtained for a torso portion of the subject. The scan may show portions of subject's torso including, but not limited to, heart, bowel gas, connective tissues, liver, kidney, skeletal muscle, fat, bone, lungs, blood and myocardium. Imaging scan data is obtained from the imaging scan at 202 of method 200. Said imaging scan data is indicative of subject's torso's cardiac geometry. In an embodiment, imaging scan may be segmented for cardiac section as well as different other organs and tissue in torso region is computed. The imaging data may be utilized for computing a geometric torso cardiac model (including volume model with heart and torso) of the subject.

In an embodiment, a plurality of electrode configurations may be incorporated on the geometric torso cardiac model. The plurality of electrode configurations may include, for example, standard configurations (apex-posterior), and proposed configurations including front back, side-side and apex anterior configurations. At 204, method 200 includes simulating a plurality of biophysical models of a Wearable Cardiac Defibrillator (WCD) such that each biophysical model of the plurality of biophysical models includes a distinct configuration (from amongst the plurality of electrode configurations) of a set of electrodes. The set of electrodes are capable of measuring shock voltages from myocardium of the subject's torso using the imaging scan data.

At 206, method 200 includes modeling, for each of the plurality of biophysical models, myocardial potential gradient (M) by using a Finite Element method (FEM), wherein the myocardial potential gradient is indicative of an effect of voltages applied at the set of electrodes during defibrillation. The biophysical simulation is explained in detail below.

The steady state electrical potential in a homogeneous volume conductor is defined as $\nabla.(\sigma\nabla\varnothing)=0$, where $\sigma$ is the conductivity tensor field and $\varnothing$ is the electric potential. Dirichlet boundary condition is applied where electric potential is known, expressed as $\varnothing(x,y,z)|_{\Omega k}=V_k$, where $V_k$ is the known potential of electrode k, and ilk specifies the domain coincident with electrode k. Neuman boundary on areas of boundary not defined by $\Omega$, expressed as $$\frac{\partial\phi}{\partial n}|_{\Omega}=0.$$

In defined geometry, this problem can be solved via analytical expansions. However, in complex geometries such as realistic torso models, numerical solutions like Finite Element Method (FEM) must be applied. The Finite element method begins by subdividing the geometry into a set of volume elements with vertices at a set of nodes, and then approximating the potential in the volume by a basis expansion: $\overline{\varnothing}(x,y,z)=\Sigma\varnothing_i N_i(x,y,z)$ where $N_i$ are a set of basis functions, one for each node in the volume element discretization, and $\emptyset_i$ are the corresponding (unknown) coefficients at those nodes. This is solved by 'Galerkin' method. Manipulation of the resulting integral equations yields: $\nabla.(\sigma\nabla\Sigma\emptyset_i N_i)=0$ Integrating on both side results in the 'weak PDE' form: $\int_\Omega \nabla.(\sigma\nabla N_i \Sigma_i \emptyset_i N_i) N_j dV = \int_\Omega 0.\nabla N_j dV$ and subsequent simplification results in solution:

$$\sum_i \phi_i \int_{\Omega-\bar{\Omega}-\varpi_k} \sigma\nabla N_i \nabla N_j dV = 0 \tag{1}$$

Aforementioned equations may be solved in SCIRun environment. The electrode models defined over space Ω may be combined in the computational mesh defined by hexahedral elements. Conductivity values for the segmented region extracted from previously created 'look up table' may be projected in the mesh by sampling with linear interpolation. Potential for shock electrode (anode) may be fixed at the specified values to define the strength of the applied shock, whereas potential for ground electrode (cathode) may be defined to be 0 mV throughout.

Typically, the Defibrillation Threshold (DFT) is used to define the energy or voltage required to defibrillate a subject using a particular electrotherapy. Defibrillation efficacy can be assessed through 'Critical mass' theorem, which considers DFT value capable of changing at least 95% myocardial mass to a potential gradient of 5V=cm as the effective defibrillation index. In an example scenario, defibrillation energy was calculated using formulation $$E = \frac{1}{2}CV^2$$

where C=130 mF and V is the required voltage DFT for the particular electrode configuration. DFT value reaching the critical mass is capable of stopping the VA but the shock magnitude itself has sufficient energy to damage the myocardium. In the example scenario, the ventricular mass was calculated with a voltage gradient >30V/cm, >45V/cm and >60V/cm, to assess possible myocardial damage.

The embodiments presented herein discloses formulating a new measure by combining DFT and myocardial damage using probabilistic distribution and weighted KL divergence (KLD). An ideal distribution of myocardial voltage gradient may be defined after defibrillation by combining two exponential functions, one rising and other decaying in amplitude for below and above of a predetermined voltage gradient, respectively. At 208, method 200 includes computing, for each of the plurality of biophysical models, an ideal probabilistic distribution of myocardial voltage gradient (C) after defibrillation by combining a first exponential function rising in amplitude for below a predetermined voltage gradient and a second exponential function decaying in amplitude for above the predetermined voltage gradient. In an embodiment, the predetermined voltage gradient is 5V/cm. Herein, the distribution should be such that the required critical mass defibrillation is achieved ideally around 5V/cm mark and the decay component diminish for value >=30V/cm. The desired distribution may be modeled as:

$$y = A_1 e^{\frac{-x}{\tau_1}} \; \forall \, x \geq 5;$$

-continued and $$y = A_2 e^{\frac{-(5-x)}{\tau_2}} \; \forall \, x < 5,$$

where A is the maximum amplitude, $\tau_1$ and $\tau_2$ are the rate constants. To preserve continuity at x=5V/cm, $A_2$ is defined as:

$$A_2 = A_1 e^{\frac{-x}{\tau_1}}$$

$A_1$, $\tau_1$ and $\tau_2$ tuned to satisfy (i) the area under the distribution for 65V/cm and >5V/cm as 5% and 95% respectively, (ii) value of the function at 30V/cm is less than 2%. The representative distribution is shown as 602 in FIG. 6. Myocardial potential gradient distribution for different electrode configuration may be compared against the modeled distribution.

Considering the modeled distribution as M and the defibrillation Voltage gradient distribution as C, the divergence or the information gain from M to C can be computed using KLD. At 210, method 200 includes calculating, for each of the plurality of the biophysical models, a divergence in the distribution of the myocardial potential gradient (M) with respect to the ideal probabilistic distribution of the myocardial voltage gradient (C). Higher voltage gradient leads to greater myocardial damage, hence we have proposed the error measure reflecting the efficacy of the defibrillation (ED) using weighted KLD $$D_{KL}^{w}$$

as given in eq. (2).

Here, the weight (W=x) allows the regions with higher myocardial gradient to be penalized more in the computation of the error measure (ED). Lower the measure, lower is the difference in entropy between M and C, making the actual defibrillation function closer to the modeled or ideal one. This difference can be considered as the error between these two distributions, and provide an informative efficacy measure (ED) combining both DFT and myocardial damage information.

$$ED(C) = D_{KL}^{w}(C\|M) = \sum_{x=0}^{\infty} x \cdot C(x) \ln \frac{C(x)}{M(x)} \tag{2}$$

At 212, method 200 includes selecting a biophysical model from amongst the plurality of biophysical models based on the calculation of the divergence. An example scenario of calculation of the divergence and selection of biophysical models is described in the description below with reference to FIGS. 3-6.

Figure 3:
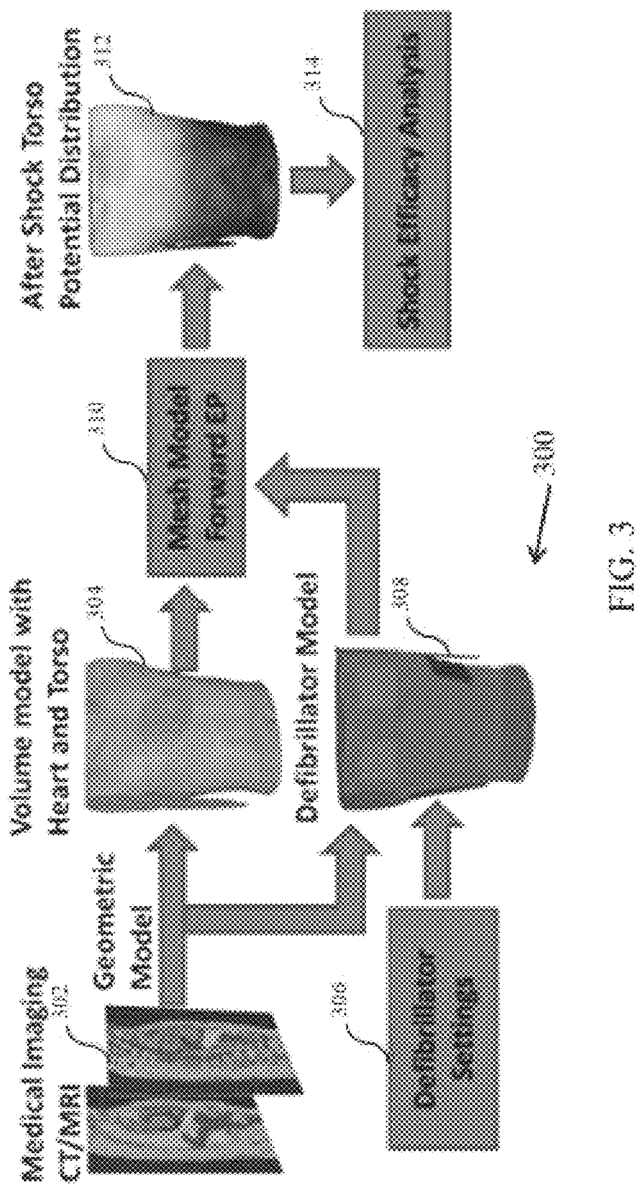
FIG. 3 illustrates a process flow diagram of a method for generating a computational model to predict and optimize defibrillation mechanism of the WCD according to some embodiments of the present disclosure.

Referring now to FIG. 3, a pipeline 300 for evaluating WCD performance is illustrated in accordance with an example embodiment. The pipeline 300 initiates with creating a 3D volume from torso-cardiac MRI slices at 302. For the purpose of experiment, MRI scan of a 19-year old healthy subject data, obtained from an open source dataset was used to create the geometric model. Image segmentation for cardiac section as well as different other organs and tissue in torso region was computed using an open source software Seg3D™. Tissue conductivity values for segmented sections were defined as per standard literature. Segmented section and their conductivity values were: bowel gas, 0.002; connective tissue, 0.220; liver, 0.150; kidney, 0.070; skeletal muscle, 0.250; fat, 0.050; bone, 0.006; lung, 0.067; blood, 0.700; and myocardium, 0.250 siemens/m. A look up table was created with segmentation index and corresponding conductivity values.

Figure 4:
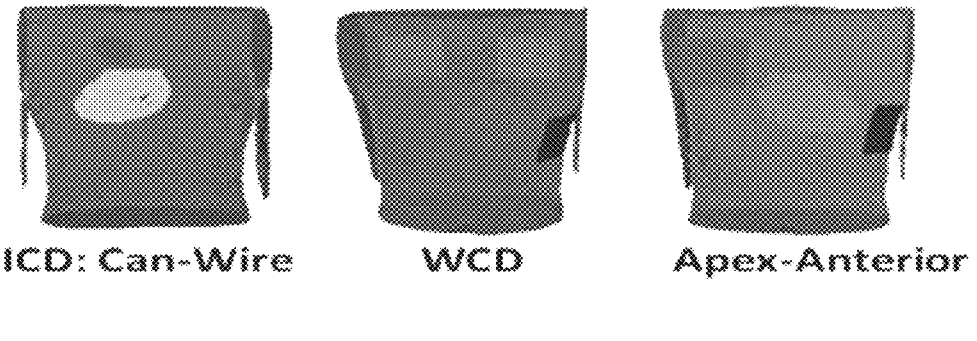
FIG. 4 illustrates electrode configurations over torso of a subject for generating a computational model to predict and optimize defibrillation mechanism, according to some embodiments of the present disclosure.
Figure 4:
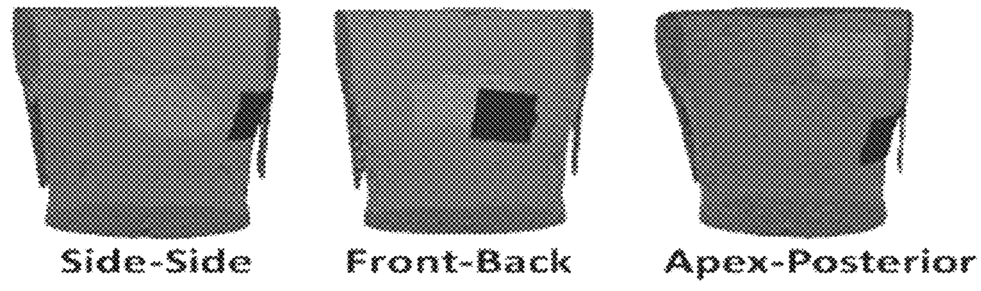

WCD specifications for modeling were incorporated from 'LifeVest WCD' (Zoll Lifecor™ Corp.). The 'shock' electrode configuration for both ICD and WCD around the torso is shown in FIG. 4. SCIRun™ software was used to incorporate electrode configuration on the geometric torso cardiac model. Electrodes in ICD simulation represents standard 'Can' and 'Wire' configuration. 'Can' electrode was placed above the heart along mid sternal line and acted as the anode. 'Wire' electrode of 0.08 meter (m) length and 0.003 m width was configured as cathode. Defibrillation electrodes for WCD were all of similar shape and size (0.1 m×0.1 m). For the standard three electrode configuration, 'apex' electrode acting as anode was positioned at midaxillary line at the level of the 5th intercostal space. Cathode electrodes were placed under the left and right clavicle at the 4th intercostal level. For side configuration, both anode and cathode were placed adjacent to the sternum across the mid axillary line. Anode electrode was placed on left precordium, in-front of chest and cathode was placed on the back behind the heart in between the scapula's for the front-back configuration.

As per critical mass hypothesis, the calculated DFT reaches the 95% myocardium volume over 5V=cm requirement, guaranteeing proper defibrillation. However, there is a considerate amount of myocardium volume exposed to a dangerously high voltage gradient (>45V/cm, shown in red in FIG. 3) which is sufficient for damaging those area permanently. A major application of WCD is for patients who are awaiting ICD implantation. Primary objective there is to replicate ICD credentials. FIG. 5B illustrates the shock potential distribution for the standard 3 electrode WCD configuration along with the DFT histogram. The defibrillation threshold along with the energy levels are comparable, indicating the effectiveness of the simulation pipeline in analyzing WCD behavior. It may be noted that WCD achieves successful defibrillation with lower defibrillation energy and also the percentage of myocardial volume in higher voltage gradient zone is lower compared to standard ICD.

Four standard shocking electrode configuration were compared for WCD to analyze the effect of electrode location in Defibrillation parameter. The standard electrode configuration for 'Zoll WCD' uses two posterior shocking electrode with one apex electrode. Shock generation is through one of the posterior and the apex electrode. Other electrode configuration tested are: apex-anterior, side-side, front back and apex posterior (FIG. 4).

Table I compares all the defibrillator parameters for all ICD and WCD configurations.

TABLE I

Defibrillator Efficacy Parameters

| Config | Applied voltage | DFT | Energy | % Myo > 30 V/cm | % Myo > 45 V/cm | % Myo > 60 V/cm | ED using KLD | ED using weighted KLD |
|---|---|---|---|---|---|---|---|---|
| ICD | 500 V | 493.8 V | 15.85 J | 18.035% | 4.765% | 1.852% | NIL | NIL |
| Apex-Anterior | 500 V | 406.7 V | 10.75 J | 7.923% | 1.608% | 0.4348% | 0.315 | 5.169 |
| Side-side | 800 V | 508.8 V | 26.92 J | 16.97% | 3.54% | 1.215% | 1.130 | 32.25 |
| Front back | 500 V | 195.5 V | 2.484 J | 2.417% | 0.434% | 0.142% | 0.244 | 4.855 |
| Apex-posterior | 500 V | 321.9 V | 6.75 J | 12.351% | 1.608% | 0.90% | 0.367 | 11.09 |

FE meshes were created in the torso to help in solving the biophysical model associated with application of external fibrillation. Herein, defibrillator voltage is acting as the source at 306. Monodomain equations were used to solve the biophysical model. From the torso cardiac geometry (304), electrodes were placed in the torso for WCD and also for ICD, for an initial comparison. Effect of external voltage applied at the electrodes were captured through modified torso and cardiac potential generation at 312. Efficacy of defibrillation is calculated through DFT value based on critical mass hypothesis and also extent of myocardial damage incurred at 314. The proposed efficacy measure obtained by combining DFT and myocardial damage using a probabilistic distribution and weighted Kullback Leibler (KL) divergence was also computed.

Figure 5A:
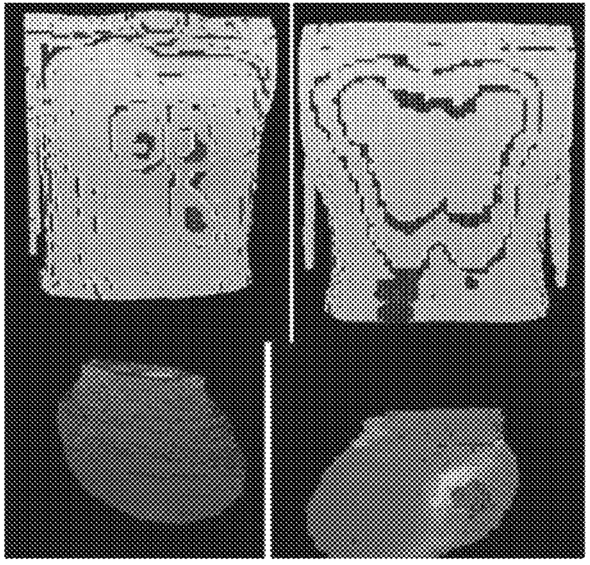
FIGS. 5A and 5B illustrate torso and cardiac potential distribution and histogram representation of myocardium voltage gradient for modeled ICD and WCD response for a subject in accordance with an example scenario.
Figure 5A:
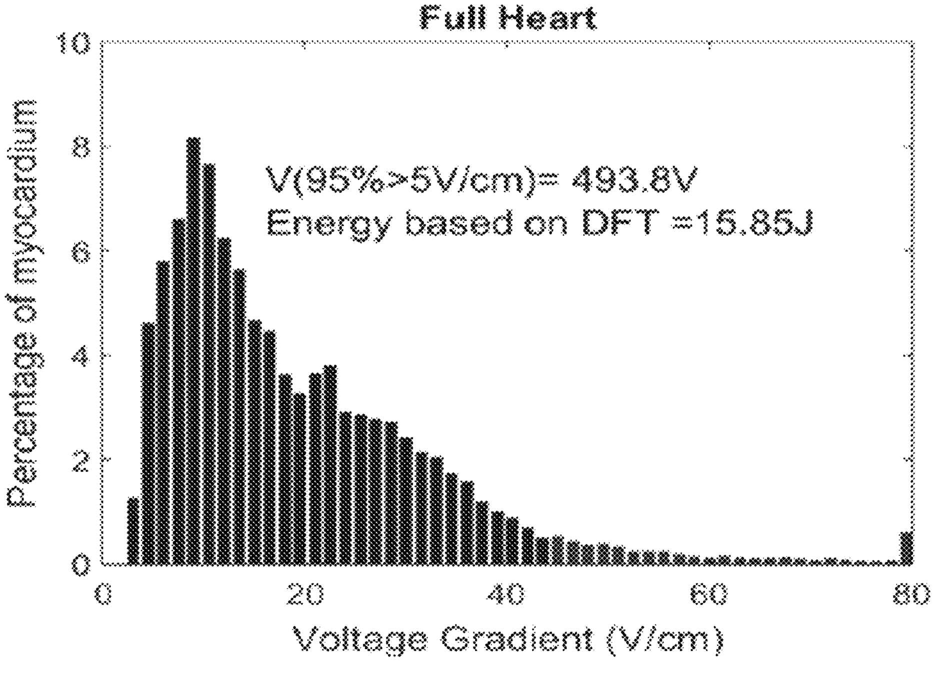
Figure 5B:
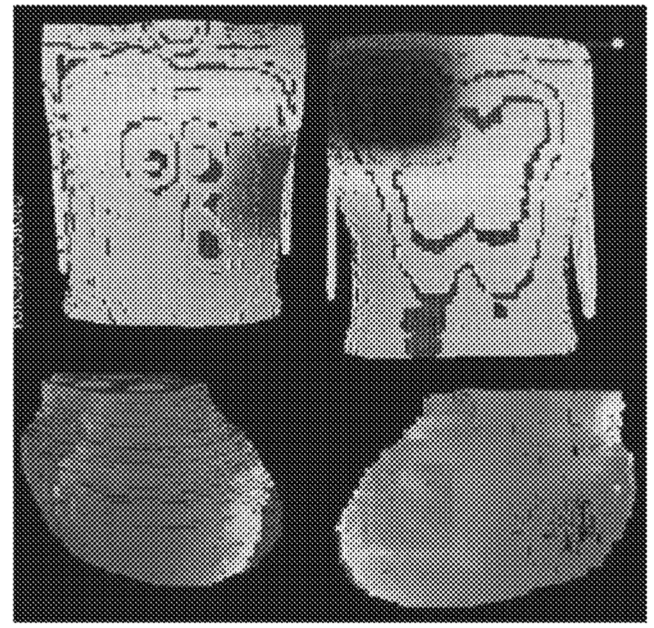
Figure 5B:
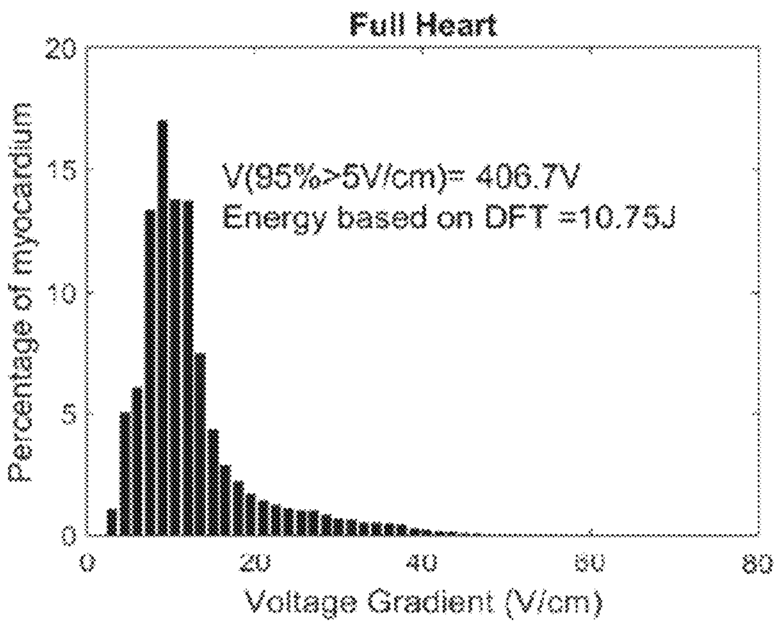

FIG. 5A shows the shock potential distribution just after defibrillation in torso and cardiac surface. Body surface potential due to normal cardiac event hardly surpasses 5 mv range, whereas during defibrillation due to the strong external voltage, cardiac potential reaches extreme depolarized state, halting the normal rhythmic propagation and resetting the myocardial potential. DFT histogram shows the percentage distribution of myocardium against the voltage gradient.

Figure 6:
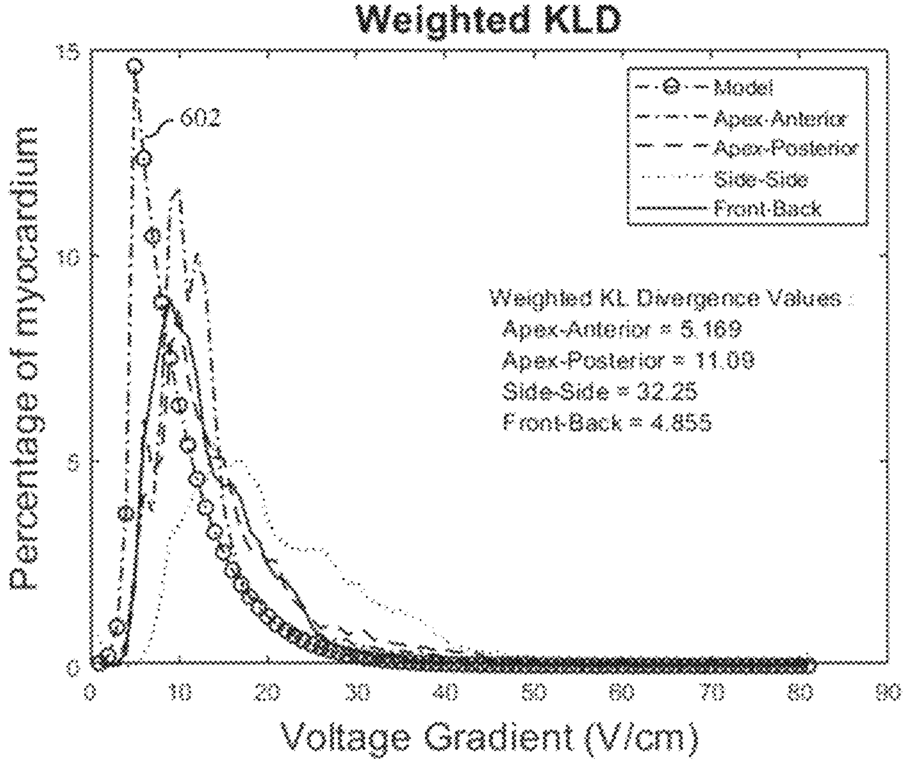
FIG. 6 shows an ideal (Model) potential gradient distribution (A1=0.3357, $\tau_1$=6; $\tau_2$=0.73, plotted in percentage scale) along with distribution for the four different WCD configuration and the associated ED error in accordance with an example scenario.

FIG. 6 shows the ideal (Model) potential gradient distribution (A1=0.3357, $\tau_1$=6; $\tau_2$=0.73, plotted in percentage scale) along with distribution for the four different WCD configuration and the associated ED error. It is evident from the DFT value, defibrillation energy and ED error measure, that different electrode configurations result in substantially different DFTs for a particular torso. Side-side configuration of electrode is generally the most convenient location to fit in defibrillator vests, however, analysis shows that this particular configuration has the maximum voltage requirement, highest DFT and energy requirement among the other configurations and a greater possibility of myocardium damage. Between ED error using KL and weighted KL, due to the variable scaling of the distribution, configurations that has higher myocardial damage are penalized more heavily, thus generating a large error value.

As indicated from the table, front-back configuration provides the best result, both in terms of DFT energy and myocardial damage index followed by apex-posterior configuration. The FE analysis with changeable electrode configuration provided an understanding on the defibrillator efficacy parameter variation with change in shocking configuration. This pipeline in general can be used for subject specific analysis and provide personalized WCD vest as per the anatomy of the patient. Location of the apex and posterior or anterior section may also vary, varying the defibrillator parameters. This is particularly true for obese subjects or pediatric users where use of standard configuration may provide successful defibrillation but at the cost of higher myocardial damage.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

Various embodiments described herein provides a computational model to predict and optimize defibrillation mechanism of a WCD. Cardiac defibrillators are lifesaving therapeutic device with potentially harming capacity if not tuned properly. With the growing demand of WCD, creation of a personalized energy distribution model based on patient's anatomy, rather than a 'one size fits all' approach, is the need of the hour. The disclosed computational model (embodied in the disclosed system 100) compares the efficiency of standard and nonstandard WCD electrode placement in the torso vest, demonstrating significant differences in defibrillation efficacy associated with different strategies. The disclosed embodiments present a new measure for performing such a comparison which combines the DFT and extend of myocardial damage. Proposed approach of tuning defibrillation parameter can also be coupled to a physical cardiac model. This may enable therapeutic device validation, combining VA detection along with the proposed optimized tuning strategy.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software processing components located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A processor-implemented method for generating a computational model to predict and optimize defibrillation mechanism of a Wearable Cardiac Defibrillator (WCD), comprises:

obtaining imaging scan data associated with subject's torso, the imaging scan data indicative of subject's torso cardiac geometry, via one or more hardware processors;

simulating a plurality of biophysical models of the WCD via the one or more hardware processors, each biophysical model of the plurality of biophysical models comprising a distinct configuration of a set of electrodes, wherein the set of electrodes are capable of measuring shock voltages from myocardium of the subject's torso generated in response to defibrillation using the imaging scan data;

modeling, for each of the plurality of biophysical models, myocardial potential gradient (M) by using a Finite Element method (FEM) via the one or more hardware processors, wherein the myocardial potential gradient is indicative of an effect of voltages applied at the set of electrodes during defibrillation;

computing, for each of the plurality of biophysical models, a probabilistic distribution of myocardial voltage gradient (C) after defibrillation by combining a first exponential functions rising in amplitude for below a predetermined voltage gradient and a second exponential function decaying in amplitude for above the predetermined voltage gradient via the one or more hardware processors;

calculating, for each of the plurality of the biophysical models, a divergence in the distribution of the myocardial potential gradient (M) with respect to the probabilistic distribution of the myocardial voltage gradient (C) via the one or more hardware processors, wherein the divergence comprises a combination of DFT and myocardial injury in a probabilistic model, and the divergence comprises a Weighted Kullback Leibler divergence (KLD); and selecting, via the one or more hardware processors, a biophysical model from amongst the plurality of biophysical models based on the calculation of the divergence.

2. The processor implemented method of claim 1, wherein obtaining the imaging scan data comprises performing image segmentation on imaging scan of the subject for cardiac section and a plurality of organs and tissue in torso region.

3. The processor implemented method of claim 1, wherein the electrode configurations comprises an apex posterior configuration, a side-side configuration, a front-back configuration and an apex anterior configuration.

4. The processor implemented method of claim 1, wherein modeling the myocardial potential gradient (M) by using the Finite Element method (FEM) for each of the plurality of biophysical models by subdividing a geometry into a set of volume elements with vertices at a set of nodes, and approximating the potential in the volume by a basis expansion including a set of basis functions, one for each node in the volume element discretization, and corresponding coefficients at each of the nodes by solving a Galerkin method where manipulation of resulting integral equation yields a value of 0, and performing integration on both side of the resulting integral equation and with subsequent simplification results in a solution.

5. The processor implemented method of claim 1, wherein the weighted KLD is computed by using the following equation:

$$ED(C) = D_{KL}^{w}(C\|M) = \sum_{x=0}^{\infty} x \cdot C(x) \ln \frac{C(x)}{M(x)}$$

wherein x represents a weight w=x which is applied to regions with a higher myocardial gradient in computation of a error measure (ED).

6. A system for generating a computational model to predict and optimize defibrillation mechanism of a Wearable Cardiac Defibrillator (WCD), comprising:

a memory storing instructions;

one or more communication interfaces; and one or more hardware processors coupled to the memory via the one or more communication interfaces, wherein the one or more hardware processors are configured by the instructions to:

obtain imaging scan data associated with subject's torso, the imaging scan data indicative of subject's torso cardiac geometry;

simulate a plurality of biophysical models of the WCD, each biophysical model of the plurality of biophysical models comprising a distinct configuration of a set of electrodes, wherein the set of electrodes are capable of measuring shock voltages from myocardium of the subject's torso generated in response to defibrillation using the imaging scan data;

model, for each of the plurality of biophysical models, myocardial potential gradient (M) by using a Finite Element method (FEM), wherein the myocardial potential gradient is indicative of an effect of voltages applied at the set of electrodes during defibrillation;

compute for each of the plurality of biophysical models, a probabilistic distribution of myocardial voltage gradient (C) after defibrillation by combining a first exponential functions rising in amplitude for above a predetermined voltage gradient and a second exponential function decaying in amplitude for below the predetermined voltage gradient;

calculate, for each of the plurality of the biophysical models, a divergence in the distribution of the myocardial potential gradient (M) with respect to the probabilistic distribution of the myocardial voltage gradient (C), wherein the divergence comprises a combination of DFT and myocardial injury in a probabilistic model, and the divergence comprises a Weighted Kullback Leibler divergence (KLD); and select a biophysical model from amongst the plurality of biophysical models based on the calculation of the divergence.

7. The system of claim 6, wherein to obtain the imaging scan data, the one or more hardware processors are configured by the instructions to perform image segmentation on imaging scan of the subject for cardiac section and a plurality of organs and tissue in torso region.

8. The system of claim 6, wherein the electrode configurations comprises an apex posterior configuration, a side-side configuration, a front-back configuration and an apex anterior configuration.

9. The system of claim 6, wherein to model the myocardial potential gradient (M) by using the Finite Element method (FEM) for each of the plurality of biophysical models; by subdividing a geometry into a set of volume elements with vertices at a set of nodes, and approximating the potential in the volume by a basis expansion including a set of basis functions, one for each node in the volume element discretization, and corresponding coefficients at each of the nodes by solving a Galerkin method where manipulation of resulting integral equation yields a value of 0, and performing integration on both side of the resulting integral equation and with subsequent simplification results in a solution.

10. The system of claim 6, wherein the weighted KLD is computed by using the following equation:

$$ED(C) = D_{KL}^{w}(C\|M) = \sum_{x=0}^{\infty} x \cdot C(x) \ln \frac{C(x)}{M(x)}.$$

wherein x represents a weight w=x which is applied to regions with a higher myocardial gradient in computation of a error measure (ED).

11. One or more non-transitory machine readable information storage mediums comprising one or more instructions which when executed by the one or more hardware processors cause:

obtaining imaging scan data associated with subject's torso, the imaging scan data indicative of subject's torso cardiac geometry, via the one or more hardware processors;

simulating a plurality of biophysical models of the WCD via the one or more hardware processors, each biophysical model of the plurality of biophysical models comprising a distinct configuration of a set of electrodes, wherein the set of electrodes are capable of measuring shock voltages from myocardium of the subject's torso generated in response to defibrillation using the imaging scan data;

modeling, for each of the plurality of biophysical models, myocardial potential gradient (M) by using a Finite Element method (FEM) via the one or more hardware processors, wherein the myocardial potential gradient is indicative of an effect of voltages applied at the set of electrodes during defibrillation;

computing, for each of the plurality of biophysical models, a probabilistic distribution of myocardial voltage gradient (C) after defibrillation by combining a first exponential functions rising in amplitude for above a predetermined voltage gradient and a second exponential function decaying in amplitude for below the predetermined voltage gradient via the one or more hardware processors;

calculating, for each of the plurality of the biophysical models, a divergence in the distribution of the myocardial potential gradient (M) with respect to the probabilistic distribution of the myocardial voltage gradient (C) via the one or more hardware processors, wherein the divergence comprises a combination of DFT and myocardial injury in a probabilistic model, and the divergence comprises a Weighted Kullback Leibler divergence (KLD); and selecting, via the one or more hardware processors, a biophysical model from amongst the plurality of biophysical models based on the calculation of the divergence.

* * * * *